(12) United States Patent
Liu et al.

(10) Patent No.: US 8,673,388 B2
(45) Date of Patent: Mar. 18, 2014

(54) METHODS OF MANUFACTURING DRUG-LOADED SUBSTRATES

(75) Inventors: Jian-Lin Liu, Bloomington, IN (US); Bruce J. Demars, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 167 days.

(21) Appl. No.: 12/878,862

(22) Filed: Sep. 9, 2010

(65) Prior Publication Data

US 2011/0071478 A1 Mar. 24, 2011

Related U.S. Application Data

(60) Provisional application No. 61/240,742, filed on Sep. 9, 2009.

(51) Int. Cl.
*B05D 3/00* (2006.01)
*A61M 25/00* (2006.01)

(52) U.S. Cl.
USPC ........... 427/2.28; 427/2.1; 427/2.24; 604/264

(58) Field of Classification Search
USPC ................ 427/2.1–2.31; 118/716; 604/264
See application file for complete search history.

(56) References Cited

U.S. PATENT DOCUMENTS

| | | | |
|---|---|---|---|
| 3,434,869 A * | 3/1969 | Davidson | 604/266 |
| 4,598,006 A | 7/1986 | Sand | |
| 5,217,493 A * | 6/1993 | Raad et al. | 623/11.11 |
| 5,340,614 A | 8/1994 | Perman et al. | |
| 5,567,769 A | 10/1996 | Shine et al. | |
| 5,624,704 A | 4/1997 | Darouiche et al. | |
| 5,670,614 A | 9/1997 | Roby et al. | |
| 5,820,607 A | 10/1998 | Tcholakian et al. | |
| 5,853,745 A | 12/1998 | Darouiche | |
| 5,902,283 A | 5/1999 | Darouiche et al. | |
| 5,968,654 A | 10/1999 | Sawan | |
| 6,217,614 B1 | 4/2001 | Fages et al. | |
| 6,413,539 B1 | 7/2002 | Shalaby | |
| 6,479,584 B1 | 11/2002 | Nakagawa et al. | |
| 6,528,107 B2 | 3/2003 | Chinn et al. | |
| 6,610,251 B1 | 8/2003 | Kanno | |
| 6,627,246 B2 * | 9/2003 | Mehta et al. | 427/2.1 |
| 6,962,714 B2 | 11/2005 | Hei et al. | |

(Continued)

FOREIGN PATENT DOCUMENTS

| | | |
|---|---|---|
| EP | 0405284 | 1/1991 |
| EP | 405284 A2 * | 1/1991 |

(Continued)

OTHER PUBLICATIONS

"CO2 Solvent Could Ehhance Stitches," Abstract, Science & Technology Concentrates, Jul. 19, 2010, p. 32.

(Continued)

*Primary Examiner* — Cachet Sellman
(74) *Attorney, Agent, or Firm* — Woodard, Emhardt, Moriarty, McNett & Henry LLP (57) ABSTRACT

A substrate is modified by exposing the substrate to a densified fluid. The substrate may be a polymer or a metal alloy, and the densified fluid may be carbon dioxide. Uses of such substrate modification include impregnation of the substrate with one or more drugs, impregnation of microcellular particles, surface modification of the substrate, and formation of microcellular compositions.

27 Claims, 5 Drawing Sheets

Schematic diagram of the high-pressure sorption apparatus
(P-Pressure transducer, TC-Temperature controller)

(56) References Cited

U.S. PATENT DOCUMENTS

| | | | |
|---|---|---|---|
| 7,008,591 | B2 | 3/2006 | Kafesjian et al. |
| 7,081,133 | B2 | 7/2006 | Chinn et al. |
| 7,108,832 | B2 | 9/2006 | Christensen et al. |
| 7,238,363 | B2 | 7/2007 | Mansouri et al. |
| 7,311,697 | B2 | 12/2007 | Osborne |
| 2001/0003007 | A1* | 6/2001 | Chinn et al. ............... 427/2.24 |
| 2002/0025384 | A1 | 2/2002 | McClain |
| 2003/0021825 | A1 | 1/2003 | Pathak et al. |
| 2003/0044514 | A1* | 3/2003 | Richard ..................... 427/2.1 |
| 2005/0058835 | A1 | 3/2005 | Howdle et al. |
| 2005/0153055 | A1 | 7/2005 | Ammon, Jr. et al. |
| 2006/0127442 | A1 | 6/2006 | Helmus |
| 2006/0257633 | A1 | 11/2006 | Inoue et al. |
| 2007/0255004 | A1* | 11/2007 | Lohrmann et al. ........... 524/588 |
| 2008/0166266 | A1 | 7/2008 | Burns et al. |
| 2009/0087471 | A1 | 4/2009 | Shimp et al. |

FOREIGN PATENT DOCUMENTS

| | | |
|---|---|---|
| EP | 1303320 | 4/2003 |
| WO | WO 02/07785 | 1/2002 |
| WO | 02/100456 A1 | 12/2002 |
| WO | WO 03/045448 | 6/2003 |
| WO | WO 2005/000364 | 1/2005 |
| WO | 2006/063158 A2 | 6/2006 |
| WO | WO 2006063158 A2 * | 6/2006 |
| WO | WO 2007/008618 | 1/2007 |
| WO | 2008/052568 | 5/2008 |
| WO | WO 2008/154621 | 12/2008 |
| WO | WO 2009/011849 | 1/2009 |
| WO | WO 2009/112851 | 9/2009 |

OTHER PUBLICATIONS

Brochure, Cook Spectrum Catheter Catalog, Cook Incorporated, Bloomington, IN, USA.

Duarte, A.R.C., et al., "Supercritical fluids in biomedical and tissue engineering applications: a review," Intl. Materials Reviews 2009, vol. 54, No. 4, pp. 214-222.

Furno, Franck et al., "Silver nanoparticles and polymeric medical devices: a new approach to prevention of infection?", J. Antimicrobial Chemotherapy, vol. 54, No. 6, pp. 1019-1024, The British Society for Antimicrobial Chemotherapy 2004.

Hanna, Hend et al., "Long-Term Silicone Central Venous Catheters Impregnated With Minocycline and Rifampin Decrease Rates of Catheter-Related Bloodstreatm Infection in Cancer Patients: A Prospective Randomized Clinical Trial," Journal of Clinical Oncology, vol. 22, No. 15, Aug. 2004, pp. 3163-3171.

Instructions for Use, Cook Spectrum Turbo-JeCT Peripherally Inserted Central Venous Catheters with Micropuncture Peel-Away Introducers, Cook Medical Incorporated.

Jones, David S. et al., "Relationship between biomedical catheter surface properties and lubricity as determined using textural analysis and multiple regression analysis," Biomaterials, vol. 25, Issues 7-8, Mar.-Apr. 2004, pp. 1421-1428.

Kazarian, .S.G, "Polymer Processing with Supercritical Fluids," Polymer Science, Ser. C, vol. 42, No. 1, 2000, pp. 78-101.

Kikic, Ireneo, "Supercritical impregnation of polymers," Solid State and Materials Science 7 (2003) pp. 399-405.

Libsack, Craig V. et al., "Role of catheter surface morphology on intravascular thrombosis of plastic catheters," Journal of Biomedical Materials Research, vol. 13, Issue 3, pp. 459-466, May 1979.

Page from Brochure, "Reactive Silicones" Brochure, Gelest, Inc., p. 35.

Raad, Issam et al., "Antibiotics and Prevention of Microbial Colonizaton of Catheters," Antimicrobial Agents and Chemotherapy, vol. 39, No. 1, 1995, pp. 2397-2400.

Reverchon, E., "Production of controlled polymeric foams by supercritical $CO_2$," Journal of Supercritical Fluids, vol. 40,, Issue 1, Feb. 2007, pp. 144-152.

Sabirzyanov, A.N., "Supercritical Fluid Extraction of Ethylene Oxide From its Aqueous Solution," Kazan State Tecnological University.

Tebbs, S.E., "Influence of surface morphology on in vitro bacterial adherence to central venous catheters," British Journal of Anaesthesia 1994; 72:587-591.

White, L.J. et al., "Mechanical and Morphological Studies of Supercritical Fluid Foamed Poly(D,L-Lactic Acid) Scaffolds," European cells and Materials, vol. 16, Suppl. 3, 2008 p. 95.

Powell et al., "Chemotherapeutic implants via subcritical CO2 modification", vol. 28, No. 36, Oct. 22, 2007, pp. 5562-5569.

Powell et al; "Chemotherapeutic implants via subcritical CO2 Modification"; Biomaterials, Elsevier Science Publishers BV., Barking, GB; vol. 28, No. 36; Oct. 22, 2007 pp. 5562-5569.

* cited by examiner

Figure 1: Schematic diagram of the high-pressure sorption apparatus
(P-Pressure transducer, TC-Temperature controller)

Figure 2

Tubes made of Pellethane Polyurethane (left), impregnated with Minocycline (middle), and with Minocycline+Rifampin (right)

Figure 3

Tubes made of carbothane PC-3595A-B20 (far left), impregnated with Minocycline (middle), and with Minocycline+Rifampin (right)

METHODS OF MANUFACTURING DRUG-LOADED SUBSTRATES

REFERENCE TO RELATED APPLICATIONS

The present application claims the benefit of U.S. Provisional Patent application Ser. No. 61/240,742 filed Sep. 9, 2009 entitled "Method of Substrate Modification Utilizing a Densified Fluid" which is hereby incorporated by reference in its entirety.

BACKGROUND

1. Technical Field

The present application relates generally to methods for modifying a substrate by exposing the substrate to a densified fluid under controlled conditions, in order to enhance selected properties of the substrate. More particularly, the application relates to method for modifying a polymer, or a metal alloy, by exposing the polymer or alloy to densified $CO_2$ under subcritical and/or supercritical conditions, and impregnating the substrate with a drug compound.

2. Background Information

In the recent past, densified fluid technology has been the focus of numerous research and development studies based on the fundamentals of high-pressure phase behavior of materials. The technique has been well developed, both in fundamental understanding and numerous commercial applications since at least the late 1980s.

A densified fluid, as referred to herein, is a fluid maintained in the vicinity of the critical point of the fluid. Due to their liquid-like solvation power and gas-like mass transfer properties, these fluids are unique solvents for uses such as synthesis, extraction and separation. Processes utilizing such solvents may generally be carried out at moderate temperatures, thereby making the processes suitable for use with many heat-sensitive compounds, such as pharmaceutical drugs. In addition, the products resulting from such processes are generally free of residual solvents. This feature is particularly beneficial in, e.g., the pharmaceutical and medical device fields, due to strict limits on the residual solvent content of the resulting products.

The critical temperature of a compound is defined as the temperature above which the pure gaseous component cannot be liquefied regardless of the pressure applied, while the critical pressure is defined as the gas or vapor pressure at the corresponding critical temperature. The temperature and pressure at which the gas and liquid phases become indistinguishable is known as the critical point. If the conditions exceed the critical points, the densified fluid exists as a supercritical fluid (SCF). If either, or both, of the temperature and pressure of the fluid are slightly below the critical points, and the densified fluid remains in a fluid state and denser than a typical gas, the densified fluid exists in a state referred to herein as a subcritical fluid (SBCF). In some cases, a subcritical fluid is at about 95% or more of its critical temperature and/or 95% or more of its critical pressure. In other cases, either, or both, of the critical temperature and critical pressure may vary by a greater amount from the respective critical temperature or pressure of the fluid. A densified fluid as referred to herein may comprise a fluid existing as either a supercritical fluid or a subcritical fluid.

In the SCF region, the physical properties of a substance are remarkable and intermediate to both liquid and gas. Near the critical point of a fluid, changes in pressure or temperature may significantly alter the physical-chemical properties (e.g., density, diffusivity, or solubility characteristics) of the densified fluid. This can be particularly important in instances in which processing conditions are sensitively manipulated, such as in drug processing. Although many compounds are capable of existing as a SCF or a SBCF, carbon dioxide is a particularly attractive compound for such use. Carbon dioxide is inexpensive, and poses little threat to the environment or human health in the amounts used as a SCF or a SBCF (e.g., as $SCCO_2$ or $SBCCO_2$). Other fluids that are capable of use as a SCF or SBCF in various applications include methane, ethane, propane, argon, nitrous oxide and water. These fluids have been utilized as supercritical fluids for applications as diverse as extraction, inorganic/organic synthesis, catalysis, material processing, and even dry-cleaning.

It is desired to utilize densified fluid technology to impregnate a substrate, e.g., with one or more drug compounds.

SUMMARY

In certain aspects, the present invention relates to strategies for loading pharmaceutical agent(s) such as antibiotic agent(s) into a substrate utilizing densified fluid as a carrier for the agent(s). The substrate can be a polymeric substrate, such as polymeric catheter tubing, and can be comprised of an elastomer, such as a thermoplastic polyurethane elastomer or silicone elastomer. In certain embodiments, portions of the substrate can be effectively masked during treatment with the densified fluid to inhibit loading of the masked regions with the pharmaceutical agent(s). The masked regions can subsequently be bonded to a device component, such as a catheter hub where the substrate is catheter tubing. Process embodiments can involve the treatment of solid drug substances with a first volume densified fluid to reduce their particle size by partial dissolution and/or fragmentation, followed by dissolution and uptake of all or part of the particles in a second volume of densified fluid and ultimately delivery into the substrate. Additionally or alternatively, process embodiments can involve the maintenance of undissolved amounts of pharmaceutical agent(s) in contact with the densified fluid during impregnation of the substrate such that additional amounts of the pharmaceutical agent(s) can be solvated by the densified fluid as initially-solvated amounts are impregnated in the substrate. Additionally or alternatively, process embodiments can include a plurality of (two or more) sequential treatments of the substrate with a densified fluid substantially saturated with the pharmaceutical agent(s), which has been discovered to provide unexpected efficacy in loading of the pharmaceutical agent(s) in the substrate at high levels. Additionally or alternatively, the substrate can be preconditioned with a penetrating agent prior to contact with the densified fluid containing the pharmaceutical agent(s), for example to provide a higher level of loading of the substrate with the agent(s) than that achieved without the preconditioning step.

Further embodiments of the invention provide unique catheters loaded with pharmaceutical agent(s). In particular embodiments, the catheters are loaded with one or more antibiotic agents, such as rifampin, minocycline, or a combination including these, and/or the catheters are comprised of thermoplastic elastomer catheter tubing, such as thermoplastic polyurethane elastomer or silicone elastomer.

Still further embodiments of the invention, as well as features and advantages thereof, will be apparent to those of ordinary skill in the art from the descriptions herein.

DETAILED DESCRIPTION

For the purpose of promoting an understanding of the present invention, reference will be made to embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present patent application sets forth multiple applications to which densified fluid technology may be utilized. The following discussion will primarily describe such use in connection with medical devices. Those skilled in the art will recognize, however, that the scope of the invention includes applications of the technology other than in connection with such devices.

One use of densified fluid technology comprises the impregnation of a substrate with one or more compounds in a manner that enhances the properties of the substrate. In one embodiment, the substrate comprises a medical device impregnated with one or more active compounds. In a particularly preferred embodiment, the substrate is a polymer and the active compound is a drug.

It is known in the medical device arts to impregnate medical device substrates with active compounds, such as anti-infective drugs, bio-active pharmaceuticals, etc. Impregnation of such active compounds can be described as the delivery of solutes to desired sites inside the medical device matrix. When the device is inserted into the body of a patient, the active compound elutes from the inserted device into the patient. Typically, the medical device to be impregnated is a polymer.

The conventional manner in which an active compound is impregnated in a medical device substrate is by initially dissolving the active drug molecule in an organic solvent, and thereafter exposing the medical device to the solution containing the solvent and the dissolved drug, e.g., by dipping, spraying, coating, etc. During this process the drug solute partitions from the solvent to the medical device. The solvent is thereafter removed from the impregnated device. Due to the generally hazardous nature of the residual solvents, their use, recovery, and disposal present a number of practical challenges for production.

Densified fluids, such as densified $CO_2$, are free of hazardous solvents, making them a favorable alternative in place of organic solvents. Densified $CO_2$ is a particularly preferred choice for use in the processing of pharmaceutical compounds, particularly when the retention of the bioactivity of the active component(s) in the formulation is a prerequisite for processing. When exposed to a densified fluid, such as densified $CO_2$, polymers exhibit various extents of swelling and enhanced chain mobility. Optimization of such factors, e.g., controlling the pressure and temperature at which the polymer is exposed to the densified fluid, may significantly facilitate and accelerate the ability of the polymer to receive a drug solute from the densified fluid solvent.

When impregnating a pharmaceutical compound into a medical device matrix utilizing a densified fluid solvent, the impregnation process typically includes the following general steps. Initially, one or more substrates intended for impregnation are positioned within a suitable reactor. The reactor should be of a type capable of withstanding pressures in a supercritical range. The active compound, such as a drug compound, is then introduced, e.g. via injection, into the reactor. The densified fluid, such as densified $CO_2$, is then introduced into the reactor under conditions such that the active compound is initially dispersed in the fluid, and thereafter transfers from the densified fluid to the matrix of the polymer. The densified fluid is then released from the reactor in a rapid, yet controlled, manner, such that the active compound (drug) remains trapped within the polymer matrix. As an alternative embodiment, the densified fluid may be introduced prior to the introduction of the drug compound.

If desired, the fluid may be introduced into the reactor as a SCF, and the entire impregnation may be carried out at supercritical conditions. Typical supercritical conditions for supercritical $CO_2$ ($SCCO_2$) are about 40° C. and 4000 psi, and a typical period of exposure is 1-2 hours, although it will be well understood that other conditions can also be used. Many drugs, due to their large mass and complex chemistry, tend to have limited solubility in organic solvents, as well as in supercritical fluids such as $SCCO_2$, and in subcritical fluids such as $SBCCO_2$. Other drugs exhibit significantly greater solubility in selected organic solvents than in selected supercritical or subcritical densified fluids, particularly such densified $CO_2$). Therefore, to facilitate the impregnation process, a substrate having a low Tg will promote loading of the drug. This is particularly true for elastomeric polymers such as poly(ether block urethane), poly(ether block amide), and the like. On the other hand, due to the relatively high rigidity of its polymer backbone, a substrate with a high Tg would undergo a slower impregnation. In addition, when the substrate is blended with a large amount of inorganic material, such as $BaSO_4$ or BiOCl, the rate or level of drug impregnation will also be lowered. In certain embodiments, the polymeric substrate will contain a significant portion by weight of a radiopaque solid, for example greater than 10% by weight, and often in the range of about 10% by weight to about 50% by weight. The radiopaque solid can be $BaSO_4$ or BiOCl, or another suitable material. The incorporation of such radiopaque materials (or "radiopacifiers") into catheter tubing substrates and resulting catheters as described herein provides preferred inventive embodiments.

On some occasions, it may be preferred to at least initially introduce the densified $CO_2$ into the reactor at subcritical conditions, e.g., at about 700-800 psi and 20-25° C. Due to the partial solubility of some drugs in water or aqueous systems such as those which occur in vivo, it is possible that the drugs may have a higher elution rate from the impregnated polymer than desired. The partial solubility of drugs in water or biologic aqueous systems may be countered to some extent by increasing/enhancing the drug's interaction with the polymer substrate. One way to improve this interaction is to increase the molecular dispersion of the drug into the substrate. In this case, hydrogen bonds are believed to form between the drug and the substrate. These bonds allow the drug molecule to be held much more firmly in the substrate, and therefore provide a longer profile of drug release. Molecular dispersion is believed to be enhanced when the $CO_2$ is at least initially introduced under subcritical conditions. Impregnation at subcritical conditions is less aggressive than at supercritical conditions. This affects both the solubility of drugs and the substrate polymer in the subcritical condition. Although impregnation at subcritical conditions can take longer than at supercritical conditions, the impregnation can be more homogeneous in terms of the loading of drug within the substrate.

In addition to the foregoing, subcritical $CO_2$ is known to be less aggressive toward the substrate and the drugs. Tests have shown that some drugs can be fully impregnated to a desired loading solely under subcritical $CO_2$ conditions. In such cases, there is no need to increase the conditions to the more severe supercritical state. In addition, in some instances this less aggressive approach (i.e., subcritical rather than supercritical conditions) may also result in a more homogeneous dispersion of the drug in the substrate. The duration of the reaction may vary depending upon the type of polymer exposed to the subcritical fluid (SBCF). For example, for a generally rigid polymer, such as a polyester, a longer time is favorable. For a softer grade polymer, such as a polyurethane elastomer, the reaction time can generally be shorter. Similarly, for a particular polymer (e.g., a polyurethane), a higher durometer grade of that polymer will typically be exposed to the densified fluid for a longer time than a lower durometer grade, other factors remaining the same. Generally speaking, a polymeric substrate with a lower Tg, or having a higher amorphous portion, would be favored for this process, as it is more amenable to loading under a particular set of conditions than would a substrate with a higher Tg, or having a lower amorphous portion.

Following exposure at the subcritical conditions, the reactor can be adjusted to supercritical conditions, if desired, to complete the impregnation. On these occasions, impregnation of the active compound can be carried out by exposure to the substrate at the subcritical conditions for a set period of time (such as 1-2 hours), and thereafter adjusting the conditions to the supercritical range. Initial tests have shown that merely extending the exposure time at subcritical conditions (e.g., by a factor of 5) does not result in a dramatic increase in loading of the drug in the substrate. Therefore, in at least some applications, a sequential exposure (initial exposure at subcritical conditions followed by exposure at supercritical conditions) is believed to be preferable.

A variation of this sequential reaction (from subcritical to supercritical) is to carry out the impregnation via a dual reactor system. In this system, first and second reactors are operationally linked, and separated by a valve system that allows selective communication between the two reactors.

When utilizing a dual reactor system, the active compound (e.g., the drug) is placed in the first reactor. Although typically both reactors will be capable of withstanding supercritical conditions, this need not necessarily be the case, and the first reactor need only be capable of withstanding the selected subcritical conditions. The substrates for impregnation are placed in the second reactor, which must be capable of withstanding the selected supercritical conditions.

Liquid $CO_2$ is initially introduced into the first reactor through a pump. Initially, the temperature of the first reactor is set at 20-25° C., and the pressure is set at about 700-800 psi. Those skilled in the art will appreciate that other suitable conditions outside the supercritical range for $CO_2$ may be substituted for those listed. The reaction is carried out in the first reactor for a suitable period of time, e.g., about 1-2 hours. During exposure to the $SBCCO_2$ in the first reactor, the particle size of the drug will typically decrease, and become more uniform. This may be by dissolution of portions of the particles and/or by fragmentation. In addition, the drug particles become well dispersed in the $SBCCO_2$. Further, amounts of the drug can be solvated within the $SBCCO_2$, providing a system with both solvated and undissolved amounts of the drug.

Following reaction in the first reactor, a valve between the reactors is opened, and the contents of the first reactor are pumped into the second reactor. The second reactor is maintained at supercritical conditions, such as at about 40° C. and 4000 psi. By exposing the polymers to the drug dispersed in the $SCCO_2$ for an appropriate period of time, e.g., for about 1-2 hours, higher loadings (i.e., higher concentrations and/or deeper penetration) of the drug into the polymer matrix may be achieved. In certain modes, it is believed that as solvated amounts of the drug from a substantially saturated supercritical $CO_2$ fluid are partitioned to or otherwise taken up in the polymer substrate, at least portions of the undissolved particulate drug are solvated in the $SCCO_2$, thus contributing to the maintenance of a drug-saturated fluid and an enhancement of drug loading into the polymer.

The selection of subcritical and/or supercritical conditions for impregnation may be varied as desired. Among the factors that may be considered when determining the conditions for a particular impregnation are the respective properties of the active compound, the particular substrate to be impregnated, the chemical structure and particle size of the drug, as well as the desired degree of impregnation of the drug into the substrate.

Thus, as described above, in some cases the entire impregnation may be carried out at subcritical conditions. This may be desirable, e.g., when the drugs are not capable of withstanding the more harsh supercritical conditions, or when the drugs otherwise do not well tolerate harsh reaction conditions. It may also be desirable when high loading of the drug is not required. On the other hand, in some instances it may be desired to carry out the entire impregnation at supercritical conditions. This may be desirable, e.g., when the polymer is not otherwise capable of having sufficient voids created in its matrix during subcritical exposure to the densified fluid, and/or when particularly high loadings are desired. On still other occasions, it may be desired to sequentially carry out the reaction under subcritical conditions followed by supercritical conditions. When utilizing the teachings of the present invention, those skilled in the art can optimize the conditions for impregnation of a particular substrate by one or more active compounds.

In theory, virtually any type of drug can be impregnated into a polymer substrate utilizing a densified fluid. However, the applicability of the impregnation for a desired purpose is basically determined by two general factors. The first factor is the transport rate of the drug(s) from the solvent into the base polymer. The second factor is the compatibility and stability between the drug(s) and the base polymer. This second factor includes the possible changes to or modification of the drug during separation or elution of the drug from the polymer matrix.

The swelling extent and alteration of the microstructure of the polymer upon exposure to a densified fluid, such as sub-critical or supercritical $CO_2$, depends on the chemical nature of the polymer and its ability to interact with the densified fluid. A substrate having a lesser ability to swell will generally be more difficult to impregnate with the drug than a substrate having an increased ability to swell. Thus, as stated above, highly crystalline polymers, such as PTFE, are generally of lesser suitability as an impregnating matrix due to the limited ability of these polymers to swell upon exposure to a densified fluid. On the other hand, less crystalline polymers, such as polyurethane, and/or polymers with large amorphous fractions, are more capable of swelling upon exposure to the densified fluid. Therefore, these compounds are generally of greater suitability as an impregnating matrix. Generally speaking, it is expected that drug infusion into the polymer matrix will be more pronounced in a rubbery and semi-crystalline polymer than in a crystalline one.

Non-limiting examples of suitable substrate materials included in this disclosure include elastomeric block copolymers. Specific examples include polyurethane elastomers; nylon elastomers (e.g. PEBAX series); polyolefin block copolymers; polyesters; biodegradable polymers including but not limited to PLA/PLGA and their copolymers (i.e. poly(lactic acid) ("PLA"), poly(glycolic acid) ("PGA"), or copolymers of lactic acid and glycolic acid), glycolide polymers or copolymers, polydioxanones, polymers and copolymers of polycaprolactone, polymers and copolymers of polyhydroxyalanoates; as well as silicones and other rubbers, such as polyisoprene polymers and copolymers. These materials can be formed into catheter tubing or other components as substrates for treatment herein, and in the case of bioabsorbable polymers, including those named above, the formed substrate can also be a suture in certain embodiments. The suture can be a monofilament suture, or a multifilament suture such as a braided, twisted or spun multifilament suture.

Those skilled in the art will appreciate that the technology described herein is believed to be particularly advantageous with a multitude of different drug types and classifications, which particular drugs may be readily identified by a skilled artisan without undue experimentation. The technology can be used with anti-infective drugs, bioactive pharmaceuticals, nitric oxide (NO) donors, anti-sense drugs, narcotic materials, bupivacaine, silver nanoparticles, and the like, wherein the drugs are capable of transport into the base polymer and achieving a satisfactory level of compatibility and stability with the base polymer.

In certain embodiments, the drug(s) to be loaded into the substrate will comprise one or more antimicrobial agents. The term "antimicrobial agent" as used herein means antibiotics, antiseptics, and disinfectants. Classes of antibiotics that may be used include tetracyclines (e.g. minocycline), rifamycins (e.g. rifampin), macrolides (e.g. erythromycin), penicillins (e.g. nafeillin), cephalosporins (e.g. cefazolin), other beta-lactam antibiotics (e.g. imipenem, aztreonam), aminoglycosides (e.g. gentamicin), chloramphenicol, sufonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam), or combinations thereof. Examples of specific antibiotics that can be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, nystatin, chlorhexidine, silver salts such as silver sulfadiazine, and combinations thereof. Additional candidate antibiotics for use in the methods and products described herein will be apparent to those of ordinary skill in the art.

Certain desirable embodiments of the invention will involve the loading of rifampin, minocycline, or a combination thereof, into the substrate. Rifampin is a semisynthetic derivative of rifamycin B, a macrocyclic antibiotic compound produced by the mold *Streptomyces mediterranic*. Rifampin inhibits bacterial DNA-dependent RNA polymerase activity and is bactericidal in nature. Minocycline is a semisynthetic antibiotic derived from tetracycline. It is primarily bacteriostatic and exerts its antimicrobial effect by inhibiting protein synthesis. Minocycline is commercially available as the hydrochloride salt which occurs as a yellow, crystalline powder and is soluble in water and slightly soluble in alcohol. Combinations including minocycline and rifampin, for example those utilized in the commercially available Cook Spectrum® catheters, have been found particularly beneficial.

As noted above, relatively soft polymeric substrate materials can be used in processes and products of the invention, and have been discovered to lend themselves to effective incorporation of drug(s) when carried by densified fluids such as $CO_2$. In some forms, a polymeric material used in the invention can have a Shore A hardness (ASTM D2240) of less than about 80, for example in the range of about 20 to about 80, or within the range of about 30 to about 70. Polymeric elastomers having such hardness values, and particularly thermoplastic polyurethane elastomers (e.g. block copolymers as mentioned above) or silicone elastomers, are used in certain beneficial embodiments.

In certain aspects, a substrate to be impregnated with a pharmaceutical agent(s) is contacted with a densified fluid containing both dissolved amounts of the pharmaceutical agent(s) and undissolved amounts of the pharmaceutical agent(s). In this manner, during a substrate impregnation cycle, additional amounts of the agent(s) can be solvated in the densified fluid, for example to replenish the fluid with the active(s) as prior-solvated amounts of the active(s) are taken up in the substrate. Such processes can be used where the densified fluid used in the impregnation cycle is substantially saturated with solvated amounts of the pharmaceutical agent(s) and can thus dissolve essentially no more of the agent(s) until it/they are taken up by the substrate and, by hydrogen bonding, ionic bonding, or other interactions, are effectively removed from the fluid solution. Thereupon, additional amounts of the agent(s) can be delivered into solution by dissolving some or all of the undissolved agent(s) in contact with the fluid. In these embodiments, the undissolved agents can be solids, and in particular embodiments particulate solids. Also in these embodiments, processes can be conducted in which an amount of the pharmaceutical agent(s) in excess of that which can be dissolved by an intended volume of densified fluid is charged to an impregnation chamber along with the substrate, the densified fluid volume is then generated in the chamber, and the impregnation cycle is caused to proceed under closed conditions in the chamber (with no additional fluid or active(s) added during the cycle). The densified fluid generated in the chamber will become substantially saturated with the active(s) while leaving some of the charged active(s) solids undissolved, will impregnate the substrate with the active(s), and will dissolve additional amounts of the active from the undissolved solids during the cycle, thus enabling the loading of more of the active(s) into the substrate. In a variant of such processes, a densified fluid substantially saturated with the active(s) and carrying undissolved amounts of the active(s) can be generated in a chamber separate from the impregnation chamber in which the substrate is received, and then transferred to the impregnation chamber and similarly caused to proceed through an impregnation cycle. These and other variations will be apparent to those of ordinary skill in the art from the descriptions herein.

In additional embodiments, the substrate is subjected to segmental treatment with the densified fluid, wherein the fluid carrying the pharmaceutical agent(s) is caused to permeate the substrate and then removed (e.g. by reducing pressure) to deposit amounts of the active(s) into the substrate, and then this cycle is repeated one or more times, e.g. one, two, three, four or five times. It has been discovered that such segmental treatments can be used to increase the loading of the drug in the substrate, for example as compared to a single treatment over a time period equivalent to that of the sum of the segmental treatments. In these processes, during each permeation cycle, the densified fluid can be substantially saturated with the pharmaceutical agent(s). This can be accomplished, for example, by maintaining undissolved amounts of the agent(s) in contact with the fluid (e.g. maintained in the same closed impregnation chamber) to replenish the level of solvated agent(s) to substantial saturation as amounts of the agent(s) are impregnated into the substrate. Thus, such segmented cycling can be combined with dissolved/undissolved pharmaceutical agent(s) strategies as discussed hereinabove. These processing embodiments can be of particular benefit where the pharmaceutical agent(s) have relatively low solubility in the selected densified fluid. Substantially hydrophilic, water-soluble agents, such as rifampin and minocycline, have relatively low solubility in densified $CO_2$, and thus these embodiments can be used to advantage when impregnating these types of agent(s) with densified $CO_2$.

In other aspects, it has been discovered that the substrate can be preconditioned with a penetrating agent in a fashion that renders it more susceptible to subsequent impregnation with pharmaceutical agent(s) carried in a densified fluid as described herein. The penetrating agent can be an organic liquid that permeates the substrate, especially a polymer substrate, and in some forms can cause the substrate to increase in volume (for example by 10% or more), while in other forms can avoid any significant increase in volume (e.g. less than 2%, including essentially no volume increase). Organic liquids traditionally used as solvents can be used, for example including alcohols (e.g. methanol, ethanol), ketones (e.g. acetone, methylethylketone), ethers (e.g. tetrahydrofuran), aldehydes (e.g. formaldehyde), acetonitrile, acetic acid, methylene chloride, chloroform, or combinations thereof. Other organic solvents may also be used, as will be understood by those working in the field. In addition, the penetrating agent can be a densified fluid, such as densified $CO_2$. In such processes, the substrate can first be treated with the densified fluid free from the pharmaceutical agent(s), followed by removal of the densified fluid from the substrate (e.g. by reducing pressure), treating the substrate with the same or a different densified fluid containing the pharmaceutical agent(s), and removing the fluid to leave the agent(s) impregnated in the substrate. As well, where a traditional organic solvent material (e.g. ethanol) is used to precondition the substrate, the organic solvent can be completely or partially removed prior to treatment with the agent(s)-laden densified fluid, for example by traditional drying techniques such as air drying, heated drying, etc. In situations where preconditioning organic solvent remains in the substrate, the agent(s)-laden densified fluid can also serve to drive out and thereby remove some or all of the remaining amounts of the preconditioning organic solvent from the substrate.

In any of the densified fluid processing described herein, organic liquids traditionally used as solvents can be used as a co-solvent with the densified fluid. For example, such co-solvents may be alcohols (e.g. methanol, ethanol), ketones (e.g. acetone, methylethylketone), ethers (e.g. tetrahydrofuran), aldehydes (e.g. formaldehyde), acetonitrile, acetic acid, methylene chloride, chloroform, or combinations thereof. Such co-solvents can be used in conjunction with densified $CO_2$ to increase the solubility of a given pharmaceutical agent(s) in the fluid and thereby enable enhanced levels of loading of the agent(s) in the substrate.

Figure 5:
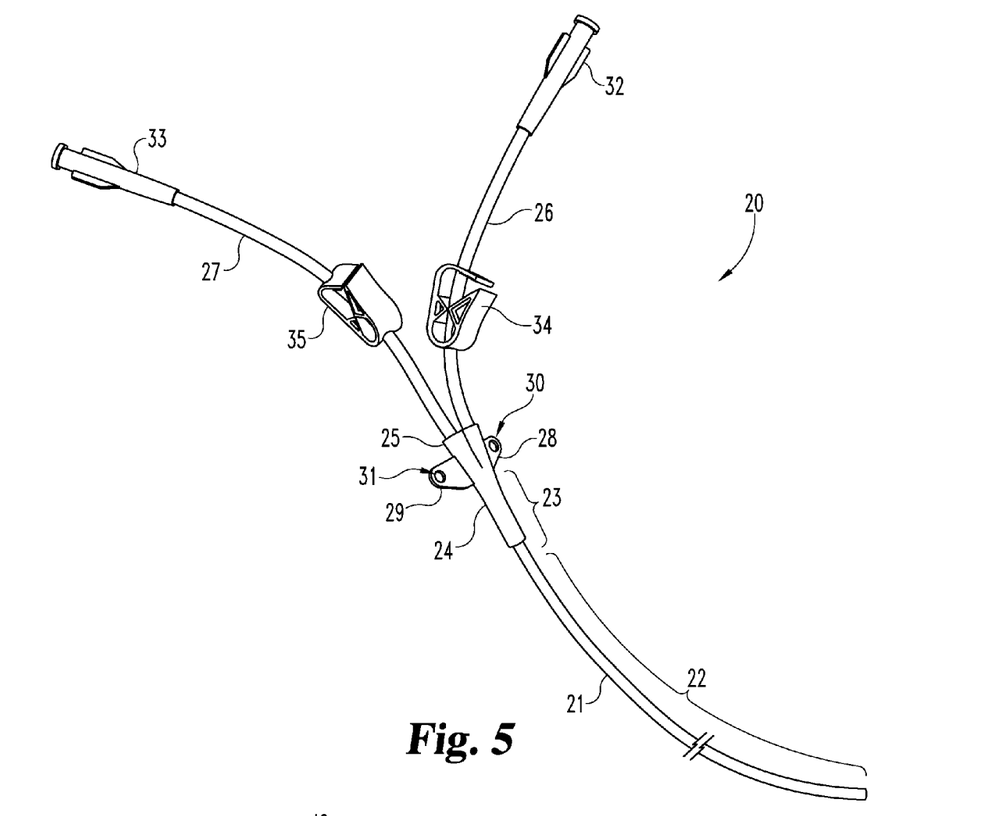
FIG. 5 is an illustration of one embodiment of a catheter in accordance with the invention.

One or more portions of the substrate to be impregnated with a pharmaceutical agent(s) can be masked to regionally inhibit impregnation in accordance with some forms of the invention. The impregnation process can be conducted, for example, in any of the ways described herein. At least one portion of the substrate, and optionally multiple portions of the substrate, has/have external surfaces that are masked with a masking element that resists penetration by the agent(s)-laden densified fluid. In this fashion, volumes of the polymeric material residing below the masking element(s) will contain lower levels of the agent(s) (an "agents-low" region), and will optionally be essentially free from the agent(s), whereas adjacent unmasked regions of the substrate will be impregnated with the active(s) as described herein. In this manner, a low-agent(s) or agent(s)-free region of the substrate can be made available for bonding of another component to the substrate, for example by heat-welding and/or using a bonding agent, with lesser or no potential interference of the bonding by the active agent(s). In some embodiments, the substrate is polymeric catheter tubing, e.g. made of any of those materials identified herein, and at least one longitudinal segment of the tubing is masked fully circumferentially during the impregnation process. A tubular masking element, such as a length of metal or polymer tube fitted over the external surface of catheter tubing, can be used for these purposes. After impregnation with the active(s), the masking element can be removed to expose the agent(s)-low or agent(s)-free external surface of the catheter tubing. In some modes of operation, due to longitudinal permeation of the densified fluid/agent(s) material through the substrate material and underneath the masking element, a transition region having increasing levels of the agent(s) in a direction from the masked region to the unmasked region can be formed. With reference to FIG. 5, in the manufacture of a catheter 20, the resulting catheter tubing 21 will have an agent(s)-loaded longitudinal segment 22 and an agent(s)-low or agent(s)-free longitudinal segment 23. Another component, such as a catheter hub 24, can be bonded over segment 23. Catheter tubing 21 can optionally define multiple inner lumens, and hub 24 can have a proximal end 25 with an equal number of openings (e.g. two, as shown) and be fitted with proximal catheter extensions 26 and 27 fluidly coupled to the respective inner lumens of tubing 21 through hub 24. Hub 24 can have laterally-extending members 28 and 29 having respective holes 30 and 31 for securing the hub 24 to skin of the patient, for example using sutures or staples, to secure the position of the catheter 20 when the agent(s)-loaded segment 22 is implanted in the patient. Catheter 20 in certain embodiments is a central venous catheter (CVC), optionally adapted as a peripherally inserted central venous catheter (PICC). Catheter 20 can also be equipped with terminal hubs 32 and 33 bonded to extensions 26 and 27, respectively, and clamps 34 and 35 fitted upon extensions 26 and 27, respectively, which can be selectively opened and closed by a user to allow and cut off fluid communication across the position of the clamps 34 and 35 on the extensions. Catheter extensions 26 and 27 can be made from the same material as or a different material from tubing 21.

In other embodiments of catheter 20, tubing 21 can be agent(s)-loaded in the segment over which hub 24 is bonded, for example being agent(s)-loaded along its full length. Otherwise, the elements and construction of catheter can be the same as discussed above. Thus, some methods of the invention can include impregnating catheter tubing 21 using any method described herein, followed by bonding hub 24 to the tubing 21 and assembling additional components of the overall catheter 20 as described above.

Still further, all or some of the components of catheter 20 can be assembled to tubing 21 at the time of impregnation. Thus, in one embodiment, unloaded tubing 21 is bonded to hub 24, and this tubing/hub construct is subject to impregnation as described herein. Hub 24 can be made from a material that is less susceptible to impregnation than tubing 21, and/or can optionally be masked during the impregnation processing. The remainder of the catheter components of catheter 20 can then be assembled to the tubing 21/hub 24 construct. These and other variations will be within the purview of those of ordinary skill in the art given the descriptions herein.

Figure 6:
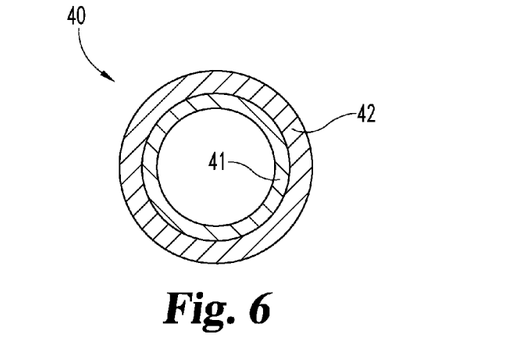
FIG. 6 shows a cross-section of a co-extruded tube in accordance with certain aspects of the invention.

In accordance with some inventive embodiments the substrate can be comprised of two or more different materials, such as polymeric materials, one or some of which is/are more susceptible to impregnation with the pharmaceutical agent(s) using the densified fluid. Advantageously, with reference to FIG. 6, in one embodiment, co-extruded catheter or other tubing 40 can have an inner polymeric wall material 41 and an outer polymeric wall material 42 that differ from one another. Inner wall material 41 can be a harder polymeric material and outer wall material 42 can be a softer polymeric material, wherein the latter is more susceptible to impregnation with the agent(s) using the densified fluid. The inner wall material 41 can thus contribute important properties, such as pushability, to the overall catheter, while the outer wall material 42 can serve as a receptive reservoir for impregnation with the pharmaceutical agent(s), and subsequent release of those agents upon implantation. Impregnation with the agent(s) can be conducted, for example, using any of the processing techniques described herein. The resulting tubing 40 can have higher levels of the pharmaceutical agent(s) in the outer layer 42 than the inner layer 41. For example, the inner layer 41 can simply have a reduced level of the agent(s) than the outer layer 42, or can be essentially free from the agent(s), depending on the materials and processing conditions selected. The resulting tubing can then be used as tubing 21 of catheter 20 (FIG. 5). The inner layer 41 and outer layer 42 can both be made from thermoplastic polyurethane elastomer (TPU), such as any of those identified herein, wherein the TPU in layer 41 has a greater hardness (e.g. as measured on the Shore A scale) than the TPU in layer 42. In still other embodiments, the inner layer 41 can be non-polymeric, for example metallic, and the outer layer can be polymeric, for example comprised of any of the polymers identified herein. In such embodiments, and in other embodiments in which an inner member is metallic and is coated with a polymeric material, the polymeric material can serve as a receptive reservoir for impregnation and eventual release of the pharmaceutical agent(s) as described herein. In some forms, the inner metallic member can be stent, such as a coronary or other vascular stent, or a strut or another portion of such a stent. An external polymeric coating is applied to the stent, strut or other portion, and the polymer-coated device is subjected to impregnation as described herein to provide a drug-releasing stent. Anti-restenosis pharmaceutical agents such as antiproliferative agents or immunosuppressive agents, e.g. paclitaxel, everolimus, or sirolimus, or analogs or derivatives thereof, can be used for these purposes.

Medical devices, such as catheters as described above, can be coated with other materials after impregnation with the pharmaceutical agent(s). For example, hydrophilic coatings can be applied to the exterior surfaces of the catheters or other devices. Hydrophilic coatings are known for these purposes, and a variety can be used. These coatings are typically hydrogels, and in certain forms can incorporate polyvinylpyrrolidone, cellulose ester, polyurethane, and/or other components. Hydrophilic coating materials such as SLIP-COAT, GLIDE-COAT, GRAFT-COAT by STS Biopolymers Inc., SLIPSKIN by MCTec, HYDRO-SLIP C by CT Biomaterials, and the like, are suitable.

In one feature of the invention, it has been discovered that impregnation processes with densified fluids, particularly densified $CO_2$, can be conducted on elastomeric polymers to provide pharmaceutical agent(s)-loaded substrates which retain highly smooth, uniform exterior surfaces. Thermoplastic polyurethane elastomers, such as those described herein, and silicone elastomers, are desirable for these purposes. Traditional solvent-based processes result in significantly more degradation of the surface properties of such materials than the densified fluid processes described herein. In certain embodiments, the substrate for the process is catheter tubing which comprises an elastomeric polymer providing an outermost surface, wherein the outermost surface remains highly smooth (having a low surface roughness) while the polymer is nevertheless loaded with significant levels of pharmaceutical agent(s).

Surface roughness can be measured or determined by methods known to those skilled in the art. For example, the roughness can be determined by optical profilometry. Instruments such as, but not limited to, the WYKO™ Profilers from Veeco Instruments Inc., Plainview, N.Y., can be employed to measure the surface roughness. For example, surface roughness can be expressed in terms of the centerline average roughness value (Ra) and/or the average maximum height of the surface profile (Rz) (also known as the "average peak-to-valley distance"), in a designated area (e.g. 100 $\mu m^2$). Additional information on such surface measurements, taken particularly on catheters, and which can be used herein can be found in S. E. Tebbs et al., *British Journal of Anaesthesia*, 1994; 72: 587-591, which is hereby incorporated herein by reference.

Illustratively, the external surface of the agent(s)-loaded catheter tubing can have a surface roughness Rz of less than about 10 μm and/or a surface roughness Ra of less than about 1.5 μm. In certain embodiments, the external surface of the agent(s)-loaded catheter tubing will have a surface roughness Rz of less than about 4 μm and/or a surface roughness Ra of less than about 0.8 μm, and in further embodiments the external surface of the agent(s)-loaded catheter tubing will have a surface roughness Rz of less than about 2 μm and/or a surface roughness Ra of less than about 0.5 μm. In certain process embodiments herein, the surface roughness of the catheter can both start (before impregnation) and finish (after impregnation) within any of these recited ranges, and/or the surface roughness (expressed in Ra and/or Rz) of the as-impregnated catheter can be no more than 130% (1.3 times) that of the corresponding surface roughness of the catheter prior to impregnated.

Catheter tubing comprised of a thermoplastic polyurethane elastomer and medical catheters such as catheter 20 (FIG. 5) incorporating such tubing are particularly beneficial from these standpoints. In particular embodiments, at least a segment of the TPU catheter tubing is impregnated with one or more antibiotic agents, such as rifampin, minocycline, a combination thereof, or any others herein identified, while having a surface roughness (Ra and/or Rz) within any of the ranges defined above, and/or while maintaining a given level of surface roughness (Ra and/or Rz) through the process within the parameters defined above. In these embodiments, at least one antibiotic agent can be incorporated in the catheter tubing at such a level that the tubing contains at least 10 micrograms per centimeter of tubing length, and/or such that the tubing is effective to provide at least a 10 millimeter zone of inhibition against a bacterium or other microorganism against which the antibiotic is effective, after immersion for 14 days in physiologic saline (0.9%), or even after immersion for 28 days in physiologic saline. In certain embodiments, rifampin and minocycline can each be incorporated in the tubing at a level of at least about 10 micrograms per centimeter of tubing length, more preferably each at a level of at least about 30 micrograms per centimeter of tubing length. Illustratively, the rifampin and minocycline can be incorporated in the catheter tubing each in the range of about 10 to about 150 micrograms per centimeter of tubing length, or each in the range of about 20 to about 100 micrograms per centimeter of tubing length. Additionally or alternatively, the rifampin/minocycline impregnated tubing can be effective to provide at least a 10 millimeter zone of inhibition against *staphylococcus epidermis* after immersion for 14 days in physiologic saline, or even after immersion for 28 days in physiologic saline. Thus, highly-loaded catheters can be provided, which retain smooth external surfaces which can beneficially resist protein deposition and bacterial adhesion, and which release antibiotic agents in a controlled fashion to provide extended inhibition of target microorgansims. Catheters and catheter tubing as disclosed herein can have any suitable gauge, with gauges of 5 to 10 French (outer diameters of about 1.6 to about 3.3 millimeters) being provided in preferred embodiments.

In addition to the impregnation of active compounds such as pharmaceutical agent(s) directly into the polymer substrate, another feature of the invention involves the impregnation of micro-encapsulated particles into the substrate. One preferred embodiment of the invention relates to the impregnation into a polymer substrate of micro-encapsulated drugs, to enable controlled release of the drug from the substrate into the bloodstream of the patient.

Micro-encapsulation refers to a process in which tiny particles or droplets are surrounded by (i.e., encapsulated within) a coating. Generally speaking, a microcapsule is a small sphere with a uniform wall or walls surrounding the sphere. The material inside the microcapsule is typically referred to as the core, internal phase, or fill. The wall is typically referred to as the shell, coating, or membrane. Most microcapsules have diameters between a few micrometers and a few millimeters. The contents of the capsule may be released by subjecting the capsule to specific conditions. For example, in the case of an enteric drug coating, the capsule dissolves by exposure to an aqueous solution at a specific pH. In other systems, the wall may be broken by other means, such as solvent action, enzyme attack, chemical reaction, hydrolysis, or slow disintegration.

Microencapsulation may be utilized to slow or otherwise control the release of a drug into the body. In this manner, one controlled release dose may be substituted for several doses of non-encapsulated drug. Such controlled release may also decrease toxic side effects for some drugs by preventing high initial concentrations in the blood. There is usually a certain desired release pattern for the microencapsulated drug. In some cases the release rate is constant, a pattern referred to as "zero-order" release. In a zero-order release pattern, the microcapsules deliver a fixed amount of drug per minute or per hour during the period of effectiveness of the drug. This release pattern can be maintained as long as the dissolving drug is maintained in the microcapsule. In this embodiment of the present invention, a drug, such as an antibiotic (e.g. any of those identified herein, or their combinations), antifungal, etc., is microencapsulated by well-known means within an outer coating to provide varied release rates for the drug. The microencapsulated drug may then be incorporated or impregnated into a polymer substrate using any of the densified fluid impregnation processes as described above.

One example of the foregoing comprises the microencapsulation of an antibiotic, e.g., rifampin, minocycline, or a combination thereof. First, the drug(s) are microencapsulated by well-known means with different coating formulations, or different amounts of a formulation, which would allow different release rates. Materials having good solubility or miscibility in $SCCO_2$ or $SBCCO_2$ are preferred. Particularly preferred examples of such materials contain functional groups of, e.g., carbonyl, ester, carbamide, fluorine, and silicone. Then, using a densified fluid, such as $SCCO_2$ or $SBCCO_2$, as the media, the microcapsules are impregnated into a polymer or porous substrate. Those skilled in the art may determine suitable reaction conditions for any particular application by taking into consideration variables such as the specific substrate, the drugs to be impregnated, the depth of impregnation, etc. In certain embodiments, a drug-containing microcapsule or other microparticle has an outer wall material with exposed functional groups, such as those identified above, and under the conditions of substrate treatment with the densified fluid in which the microcapsules or other microparticles are dispersed, portions of the wall material with the functional groups permeate the surface of the substrate. Upon removal of the densified fluid (e.g. by reducing pressure), the microcapsules or other microparticles remain coated on the surface of the substrate and bound to the substrate due to impregnation of the functionalized outer wall portions into the substrate.

Due to the varying dissolution rates of the microencapsulated antibiotic or other drug, the polymer substrate would have the ability for controlled release of the antibiotic or other drug.

Another feature of the present invention comprises impregnating a metal alloy of a type capable of undergoing a phase transition from a first generally crystalline phase at a first temperature to a second generally crystalline phase at a second temperature, and having a generally amorphous phase at a temperature between the first and second temperatures. In one embodiment, the alloy is impregnated with a drug. In a particularly preferred embodiment, the metal alloy comprises a shape memory alloy, such as nitinol.

Nitinol is a term used to refer to a family of nickel titanium alloys that contain nearly equal amounts of nickel and titanium. Nitinol has received considerable attention in the medical field for its unique properties, such as its shape memory effects. It is commonly used to form, e.g., medical wire and stents. As well known by those skilled in the art, nitinol undergoes a phase change within a predictable temperature range between a first crystalline phase (termed a martensitic phase) at a relatively low temperature, and a second crystalline phase (termed an austenitic phase) at a relatively high temperature.

Due primarily to the different nickel:titanium ratios in various nitinol alloy compositions, the temperatures at which nitinol undergoes this phase change will typically differ somewhat from one blend to another. The phase change temperature will typically range somewhere between about −200 and 100° C., more typically between about −50 and 50° C., and commonly between about −25 and 25° C. When a nitinol blend is at a temperature within its phase change range, the composition will have a generally amorphous morphology. This amorphous morphology is typically greatest at or near the midpoint of the phase change temperature range. The amorphous nature of the material at this stage indicates that free volume exists. This is in contrast to the highly crystalline structure of the material as it exists at temperatures other than within the phase change temperature range, wherein little free volume exists. A compound having an amorphous stage as described may favorably be infused at this stage by a drug or other molecule via the dense gas technology.

It is known to coat pharmaceuticals onto the surface of a medical device formed of a metal alloy, such as nitinol. When the medical device is a nitinol stent, the stent may be coated with a pharmaceutical prior to placement of the stent within a body vessel. In this case, the presence of the pharmaceutical minimizes the possibility of restenosis of the vessel following placement of the stent. In such applications, a recurring problem is achieving sufficient adhesion of the drug and/or coating to the surface of the metal alloy.

Currently, the most common method is to load the pharmaceutical into a polymer matrix, and to apply a coating of the polymer matrix having the pharmaceutical load onto the nitinol substrate. This action increases the diameter of the device, and limits release of the pharmaceutical load to a decomposition of the polymeric coating. Typically, such release occurs within a relatively short time after placement of the device into the body of the patient. Impregnating the pharmaceutical into the matrix of the nitinol stent while the nitinol is at an amorphous stage avoids the problems of the prior art associated with coating the stent. Such impregnation also would allow better loadings of the pharmaceutical, and would allow more prolonged control of the release of the drug.

According to an embodiment of the present invention, a nitinol substrate is impregnated with a pharmaceutical composition utilizing a dense gas carrier as described herein. In this case, the impregnation can be carried out at a temperature within the phase change range of the particular nitinol compound, such as at a temperature between about −200 and 100° C., more typically between about −50 and 50° C., and more preferably, between about −25 and 25° C. In theory, when the nitinol metal is undergoing the phase shift, there are "molecular voids" in the crystalline structure. These voids provide suitable space for impregnation of pharmaceuticals into the structure during this transformation stage. Once the drug is anchored into the nitinol structure, an additional process can be developed to build up or increase the thickness of the drug onto the nitinol substrate. The impregnation of the nitinol or other metal alloy in accordance with these aspects of the invention can be conducted using any of the densified fluid techniques described herein.

Another feature of the present invention comprises the formation of microcellular structures in a substrate by exposure to a densified fluid. In one embodiment, the substrate is a polymer. Preferably, the densified fluid is a supercritical fluid, such as $SCCO_2$, although a subcritical fluid may be substituted. The microcellular structures can be formed in the substrate during the same process in which the densified fluid is used to impregnate a pharmaceutical agent(s) into the substrate. In this fashion, both the physical properties of the substrate and the manner in which it releases the pharmaceutical agent(s) can be modified in the process.

Polymeric foams formed of microcellular structures have a closed-shell structure with a typical cell density between about $10^9$ and $10^{15}$ cells $cm^{-3}$. Foamed materials have superior properties when compared to unfoamed counterparts in terms of enhanced ratio of flexural modulus to density, and impact strength. The phasing out of ozone-depleting substances, mainly chlorofluorocarbons (CFCs) associated with the Montreal Protocol, acts as a substantial driver toward the use of microcellular technology.

In the preparation of polymeric foams the polymer is saturated with an inert gas, such as $CO_2$, thereby placing the matrix in a plasticized state. Rapid temperature-ramping or depressurization results in $CO_2$ escaping from the material, which can cause nucleation. The relationship of the Tg depression to pressure dictates the conditions required for cell nucleation and growth to occur.

Conventional microcellular, or foamed, polymeric structures are generally produced by incorporating a compound capable of yielding the inert gas into the molten polymer. The generation of the inert gas causes the polymer to expand, and thereby develop a microcellular structure. One well-known method for foaming a polymer in this manner involves adding a chemical blowing agent with the polymer pellets. In another method, a gas is injected directly into the melt stream of the plastic.

The method described herein takes a different approach to creating a microcellular structure than the well-known methods described above. The approach is to use a densified fluid, such as supercritical $CO_2$ or subcritical $CO_2$ as the mechanism for generating the microcellular structure.

Figure 4:
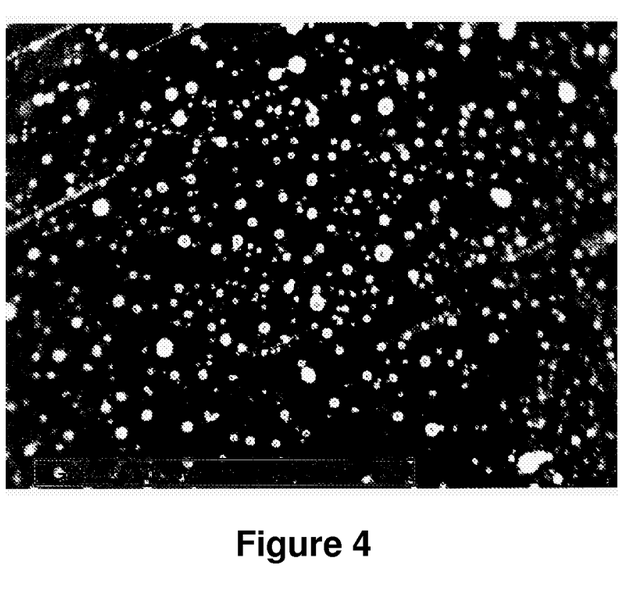
FIG. 4 is a photograph showing gas bubbles trapped inside a thin film of a polyurethane block copolymer during formation of a microcellular structure by exposure to a supercritical fluid.

In one preferred method, a suitable polymer film or catheter is first immersed in the densified fluid, e.g. $SCCO_2$, via exposure to the supercritical fluid in a suitable reactor at suitable reaction conditions. Although many polymers are suitable for forming microcellular structures, preferably the polymer will have either a high content of amorphous regions, or a low Tg (e.g., below room temperature). When supercritical $CO_2$ is used as the densified fluid, one non-limiting example of a set of suitable reaction conditions comprises 4000 psi and 40° C. for about 2 hours. Due to the high penetration power of the supercritical $CO_2$, the media can effectively penetrate the substrate. At the end of the reaction, the pressure inside the reactor is released at a rapid rate so that the $CO_2$, as a gas, is trapped inside the substrate. The release rate (pressure drop) is an important process factor that relates to the size of the cell. It also may closely relate to the substrate. FIG. 4 shows the gas bubbles trapped inside a thin film made from polyurethane block copolymer according to this process. The gas bubbles were formed while simultaneously loading minocycline into the film with the supercritical $CO_2$.

Amorphous polymers with a glass transition temperature below room temperature are especially preferred for this process, although other polymers with a glass transition temperature above room temperature may be useful in a particular application. Non-limiting examples of particularly preferred polymers include segmented block copolymers, such as poly (ether-b-amide) and poly(ether-b-urethane), as well as silicone. A more rigorous condition would typically be needed for those polymers with higher Tg and/or a more crystalline structure.

As another variation, a tube could be co-extruded with a flexible block copolymer on the outer layer and a more rigid polymer on the inner layer. The outer layer could be foamed utilizing densified $CO_2$ as described. The foamed outer layer could then be, e.g., impregnated with a pharmaceutical(s) or otherwise modified in a manner to improve a particular property of the layer. In this example, the rigid, inner layer would act as a support material.

In one example of the foregoing, tube could be co-extruded to comprise a soft grade (e.g., 70A-80A) aliphatic poly(ether-b-urethane) outer layer and a more rigid aromatic poly(ether-b-urethane) as the inner layer. The mechanical properties can be adjusted, e.g., either from the grade of the materials or the wall thickness of each of the materials.

When it is desired to provide a microcellular tubular structure having a drug dispersed therein, the drug may either be impregnated in the polymer prior to, or subsequent to, or simultaneously with, the microcellularization of the polymer. When impregnated prior to microcellularization, the impregnation may be carried out, e.g., by initially exposing the base polymer to the densified gas having the drug dispersed therein as described above. The polymer having the drug dispersed therein is then subjected to microcellularization as described.

When impregnated subsequent to microcellularization, the microcellular (foamed) structure is initially created by exposure to the densified gas as described. The foamed structure is then subjected to a second exposure to the densified gas to impregnate the drug.

When impregnated during microcellularization, the densified fluid used to create the microcells carries a pharmaceutical agent(s), such as any of those described herein, and impregnates the substrate with the agent(s) as it is removed from the substrate in a fashion that creates the microcells.

In order to promote a further understanding of certain aspects of the invention, and their features and advantages, the following specific Examples are provided. It will be understood that these examples are illustrative, and not limiting, of the invention.

Example 1

Impregnation of Polymeric Tubes and Films

Figure 1:
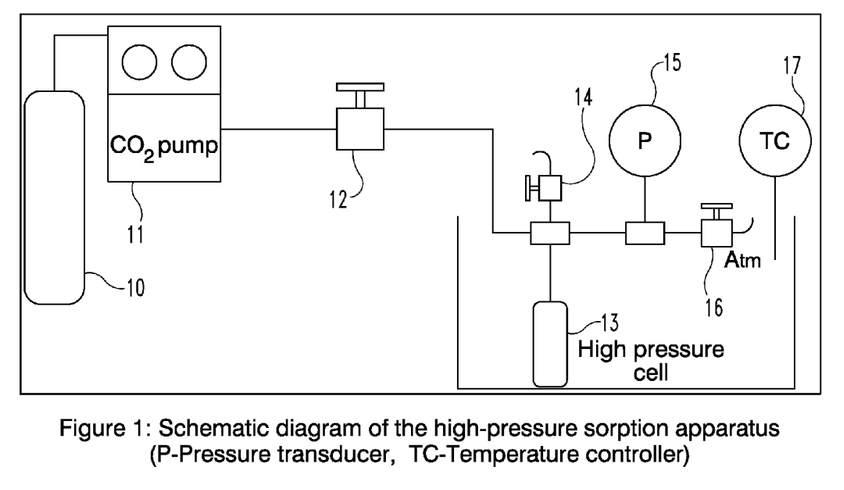
FIG. 1 is a schematic diagram of an experimental setup for modification of a substrate utilizing densified fluid technology.

One example of the use of densified fluid technology in the impregnation of a polymeric substrate with a bioactive agent is described below. In this example, polyurethane tubes were impregnated with the antimicrobial drugs rifampin and minocycline from a densified $CO_2$ solvent. Those skilled in the art will recognize that other polymer configurations, e.g., polymeric films, may be substituted for the tubes. FIG. 1 is a schematic diagram of the experimental setup for the impregnation system. A tank 10 of $CO_2$ fed to a $CO_2$ pump 11. Pump 11 fed $CO_2$ through system valve 12 and into a high pressure impregnation cell 13, in which the substrates to be impregnated were positioned. Cell 13 was equipped with a valve 14 positioned for pressure injection of materials into cell 13, if desired. The system included a pressure transducer 15 for monitoring pressure during impregnation, which was vented to atmosphere through valve 16. A temperature controller 17 controlled the temperature of the high pressure cell 13.

Initially, segments of polyurethane tubing for impregnation were placed into a suitable reactor capable of withstanding supercritical conditions, such as that described above. Two different grades of thermoplastic polyurethanes were subject to the impregnation reaction, namely PELLETHANE® 2363-80A (Shore A hardness about 80), available from Dow Chemical Co. and CARBOTHANE® PC-3595A-B20 (Shore A hardness about 90), available from Lubrizol Advanced Materials, Inc., and a separate impregnation was carried out for each. The active agent(s), either minocycline alone or minocycline+rifampin, were introduced into the reactor. In this case the reactor was equipped with a mixing shaft to enhance the mixing of the drugs and the polymer tubes during the reaction. Although the use of a mixing shaft is optional, it is believed that mixing the tubes during exposure to the densified fluid and the drugs results in a more uniform impregnation of the tubes.

High purity liquid carbon dioxide was then pumped into the reactor. The pressure and temperature of the reactions were set. Typically, the pressure will not exceed about 4000 psi, the reaction temperature will not exceed about 60° C., and the duration of the reaction will be between about one and five hours. Those skilled in the art may vary these conditions as desired for a particular application. Following completion of the reaction or impregnation cycle, the carbon dioxide was released into a ventilation hood from a needle valve.

Figure 2:
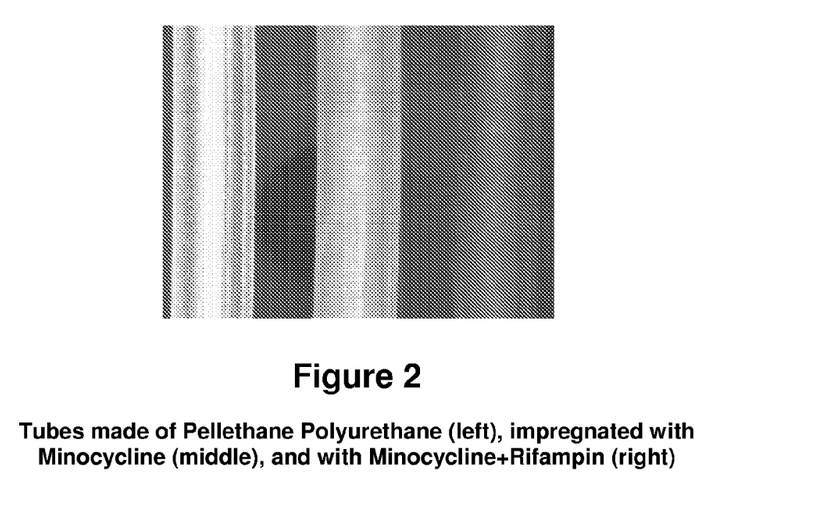
FIG. 2 is a photograph of a series of PELLETHANE® polyurethane tubes following exposure to supercritical $CO_2$, wherein a first tube is not impregnated, a second tube is impregnated with minocycline, and a third tube is impregnated with minocycline and rifampin.
Figure 3:
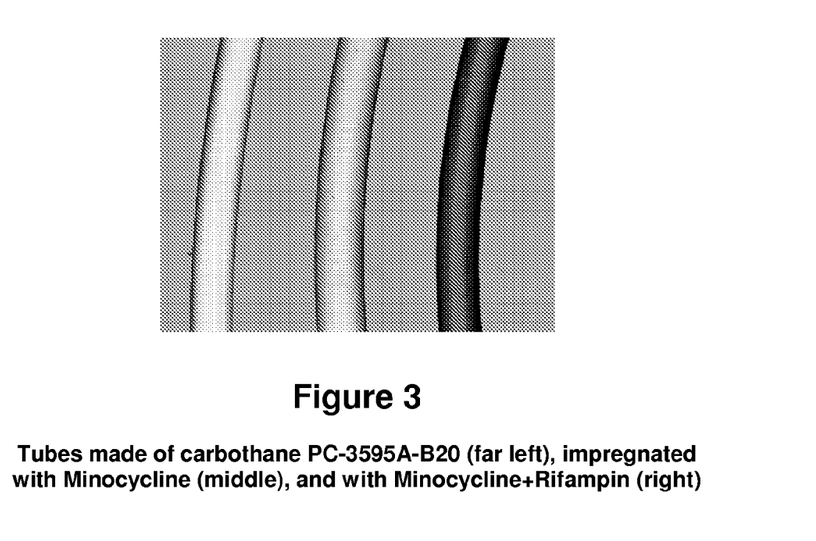
FIG. 3 is a photograph of a series of CARBOTHANE® polyurethane tubes following exposure to supercritical $CO_2$, wherein a first tube is not impregnated, a second tube is impregnated with minocycline, and a third tube is impregnated with minocycline and rifampin.

The tubes impregnated with the drugs were collected from the bottom of reactor. FIG. 2 is a photograph of a series of PELLETHANE® polyurethane tubes. FIG. 3 is a photograph of a series of CARBOTHANE® polyurethane tubes. In each figure, the first (left) tube illustrates a tube that was not exposed to the reaction. This tube has a generally yellow color. The second (middle) tube was subjected to impregnation with minocycline only. This tube has a generally orange color. The third (right) tube was impregnated with both minocycline and rifampin. This tube has a generally brown color.

The color difference between the first tube and the respective second and third tubes demonstrates the infusion of drugs into the second and third tubes through the impregnation process. The color difference between the second and third tubes demonstrates the infusion of two drugs (minocycline+rifampin) in the third tubes, and only a single drug (minocycline) into the second tubes.

Short term (one day) Zone of Inhibition tests were carried out on at least three separate samples exposed to the same treatment. These tests have shown that the densified fluid impregnation process appears to be comparable to the solvent-based impregnation systems.

Example 2

Segmental Processing

The polyurethane used in this Example was an aromatic polyether polyurethane, Pellethane 2363-83A, a block copolymer comprised of a soft segment polyether and a rigid segment aromatic polyurethane. A polymer film was made directly from pellets of the polyurethane and the film was pre-dried to a low moisture content of 0.002%. The film was placed in the impregnation reaction chamber along with amounts of the drugs rifampin and minocycline in excess of that which could be dissolved in the densified $CO_2$ through the course of the process. This facilitated the maintenance of high dissolved levels of the drugs in the system during impregnation.

In a 3 hour segmental process, the impregnation reaction was stopped at the end of each one hour segment by reducing the system pressure, and then fresh $CO_2$ was loaded and reaction started again. The reaction temperature and pressure were at 50° C. and 4000 psi. Comparative 3 hour continuous processes were performed under the same temperature and pressure conditions.

After the treatment, the film was removed from the reactor and then soaked and rinsed with distilled water for about 30 seconds to remove any drug particles on the film surface. Excess water on the film was wiped using a soft clean tissue paper. Three ¼" diameter disks were cut from the same treated film and readied for HPLC testing to determine drug content and zone of inhibition (ZOI) testing against *staphylococcus epidermis*.

Results of drug loadings and one day ZOI for film samples treated under different conditions are summarized in Table 1 below. The results show that segmental processing can be used to surprisingly and dramatically increase the level of drug loading in the substrate, and that higher reaction temperatures increase the drug loading for continuous or segmental processes.

|  | Temp (° C.) | Time (hours) | Minocycline (μg/disc) | Rifampin (μg/disc) | ZOI(mm), 1 day |
|---|---|---|---|---|---|
| Continuous | 35 | 3 | 4 | 6 | 32 |
|  | 50 | 3 | 4 | 12 | 34 |
|  | 60 | 1 | 3 | 16 | 36 |
| Segmental | 35 | 1-1-1 | 3 | 7 | 32 |
|  | 50 | 1-1-1 | 31 | 50 | 34 |
|  |  | 1-1-1 | 26 | 47 | 38 |

Example 3

Substrate Preconditioning

Radiopacifier-filled polyurethane elastomer tubing samples were evaluated in this Example. The radiopacifiers were bismuth oxy chloride (BiOCl) or barium sulfate (BaSO$_4$). Separate tube segments were used, one type made with a polycarbonate polyurethane material and another type made with a polyether polyurethane material. Samples were either soaked in ethanol prior to the impregnation reaction, or not. The length of the tubing segments was about 5 cm. Several samples (preconditioned, and not preconditioned) were placed in the reactor and minocycline and rifampin were added into the reactor as in Example 2. The reaction conditions were 50° C. and 4000 psi, processing with supercritical CO$_2$. The treated tube segments were tested for active content and (ZOI) as in Example 2.

The results are presented in Table 2 below, in which "M" represents minocycline and "R" represents rifampin. The drug loadings were almost double for tubing segments pre-soaked in ethanol at 40° C. for 30 minutes. It is believed that the ethanol acted as a good solvent to penetrate the polymer and effectively increase the "free volume" of the polymer in a fashion that facilitated the subsequent impregnation process. No ethanol was detected by smell in the preconditioned samples after the impregnation process. The dense gas CO$_2$ also served to remove the pre-soaked ethanol during the impregnation process.

TABLE 2

| | Polyether PU | | | | | | | | |
|---|---|---|---|---|---|---|---|---|---|
| | Base | | | 25% BiOCl | | | 25% BaSO4 | | |
| | M (μg/cm) | R (μg/cm) | ZOI (mm) | M (μg/cm) | R (μg/cm) | ZOI (mm) | M (μg/cm) | R (μg/cm) | ZOI (mm) |
| No soaking | 30 | 60 | 39 | | | | 13 | 45 | 30 |
| 30 minute soak in ethanol at 40° C. | 76 | 146 | 42 | 78 | 76 | 41 | 78 | 126 | 40 |
| | 77 | 112 | 44 | | | | | | |

| | Polycarbonate PU | | | | | |
|---|---|---|---|---|---|---|
| | 20% BaSO4 | | | 30% BaSO4 | | |
| | M (μg/cm) | R (μg/cm) | ZOI (mm) | M (μg/cm) | R (μg/cm) | ZOI (mm) |
| No soaking 30 minute soak in ethanol at 40° C. | 95 | 155 | 39 | 58 | 88 | 40 |

Example 4

Use of Co-Solvent with Supercritical CO$_2$

A sample of polyurethane elastomer tubing was processed for rifampin:minocycline impregnation and subsequent testing generally as described in Example 2, except that a small amount of ethanol (1 ml) was pressure injected into the impregnation reaction chamber during the early stages of the reaction. The results are shown in Table 3. The results demonstrate that co-solvents in which the rifampin and minocycline have higher solubility than the densified CO$_2$ can be used to enhance drug loading into the tubing substrates.

TABLE 3

| | Minocycline (μg/cm) | Rifampin (μg/cm) | ZOI (mm), 1 day |
|---|---|---|---|
| No co-solvent | 30 | 60 | 39 |
| 1 ml Ethanol | 74 | 46 | 38 |

Example 5

Elution Studies of Impregnated Tubing

Various thermoplastic polyurethane elastomers, extruded into catheter tubing, were subjected to varied conditions of impregnation of rifampin and minocycline with supercritical CO$_2$, using either continuous processing (preconditioned with ethanol, or not) or segmental processing as generally described in the Examples above. The materials of the tube substrates were as follows.

Sample A: Carbothane 3555D-B20 (Lubrizol)
Sample B: Tecoflex EG93A (Lubrizol)
Sample C: Pellethane 20080 (Lubrizol), loaded with BiOCl (25%)

Figure 7:
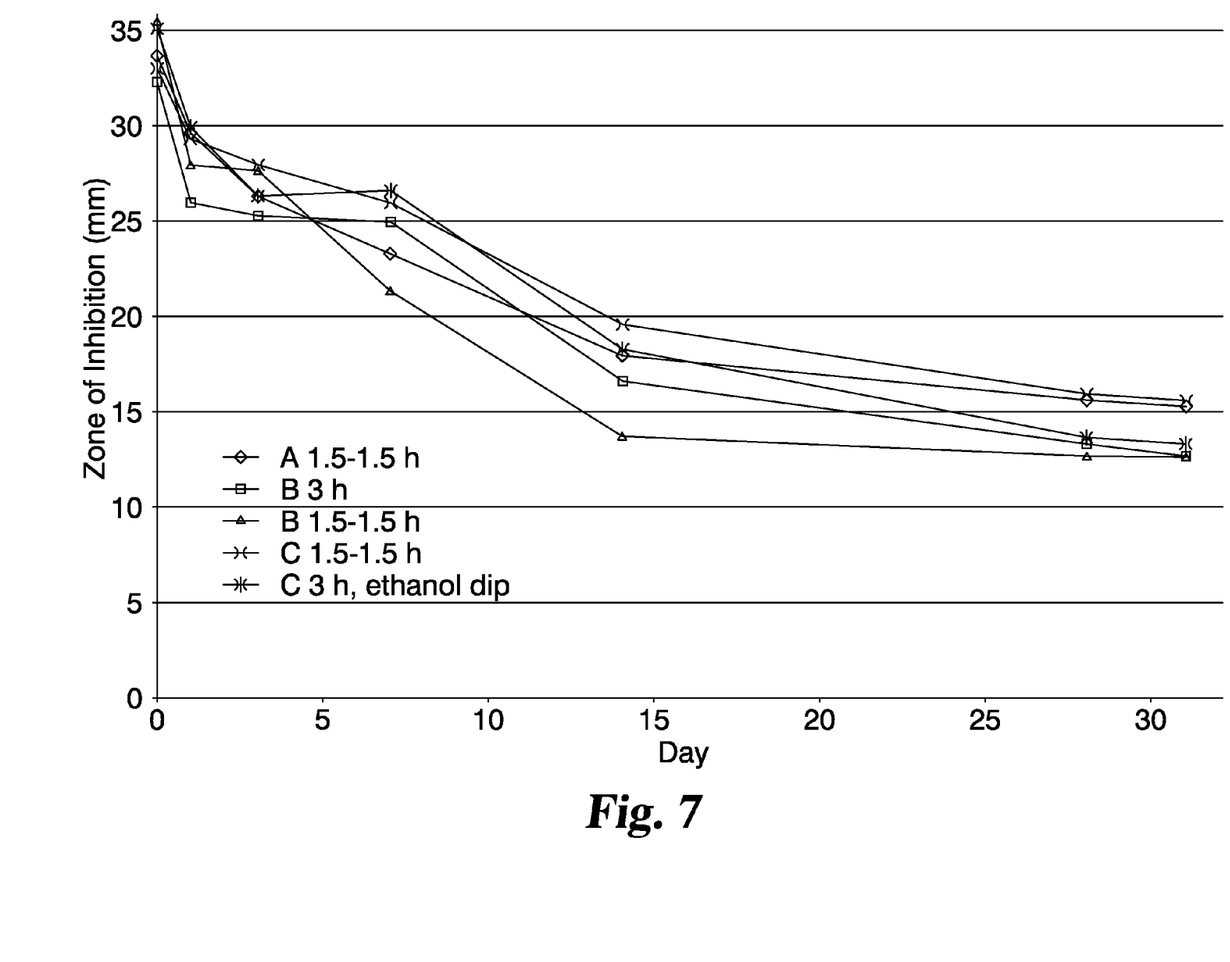
FIG. 7 provides a graph showing the results of zone of inhibition testing in accordance with Example 5 below.

Tube segments of samples A, B and C were subjected to segmental processing as described in Example 2, except using two 1.5 hour long segments. A tube segment of Sample B was also subjected to a corresponding 3-hour continuous impregnation process as described in Examples above, and a tube segment of Sample C was subjected to an ethanol preconditioning process as described in Example 3. The treated tube segments were immersed in physiologic saline (0.9%), and at various time intervals samples were cut from the segments and tested for ZOI as in the Examples above. The results are plotted in FIG. 7, and demonstrate that the drug-loaded tubing exhibited substantial ZOI's for extended periods of time after immersion in the saline.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

One advantage of the use of a densified fluid, such as $SCCO_2$, as a "temporary" plasticizer in polymer processing lies in the ability of the densified fluid to weakly interact with the backbone in polymers. This leads to a reduction of the Tg, Tm in some polymers, polymer swelling, and the facilitation of solute mass transport within polymer matrices. The specific uses of this technology discussed in this application are not intended to be exclusive, and numerous other uses of this technology are within the scope of the present invention.

Accordingly, while the invention has been illustrated and described in detail in the drawings and foregoing description, the same is to be considered as illustrative and not restrictive in character, it being understood that only certain embodiments have been shown and described and that all changes and modifications that come within the spirit of the invention are desired to be protected

The invention claimed is:

1. A method for preparing antimicrobial-releasing medical catheter tubing, comprising:
    contacting catheter tubing comprised of thermoplastic polyurethane elastomer or silicone elastomer with a densified fluid having one or more antimicrobial agents dissolved therein under conditions wherein the densified fluid permeates the catheter tubing;
    removing the densified fluid from the catheter tubing to leave amounts of the one or more antimicrobial agents impregnated in the catheter tubing; and
    dissolving additional amounts of the one or more antimicrobial agents into the densified fluid during said contacting step.

2. The method of claim 1, wherein said dissolving additional amounts includes providing undissolved solids comprising the one or more antimicrobial agents within the densified fluid, such that at least some of the undissolved solids are dissolved in the densified fluid during said contacting step.

3. The method of claim 1, wherein said one or more antimicrobial agents comprise rifampin or minocycline.

4. The method of claim 1, wherein said one or more antimicrobial agents includes a combination of rifampin and minocycline.

5. A method for impregnating a polymer substrate with a pharmaceutical agent, comprising:
    contacting the polymer substrate with a volume of densified fluid substantially saturated with one or more pharmaceutical agents, said contacting under conditions effective for impregnating the substrate with the one or more pharmaceutical agents; and
    during said contacting, maintaining undissolved amounts of the one or more pharmaceutical agents in the volume of densified fluid so as to replenish the densified fluid with additional dissolved amounts of the one or more pharmaceutical agents.

6. The method of claim 5 wherein the polymer substrate is catheter tubing.

7. The method of claim 6 wherein the catheter tubing is comprised of thermoplastic polyurethane elastomer or silicone elastomer.

8. The method of claim 5 wherein the undissolved amounts are comprised of solid particulate.

9. The method of claim 8 which comprises, prior to said contacting, charging an amount of solid particulate comprising the one or more pharmaceutical agents to a reactor, and wherein said a volume of densified fluid substantially saturated with one or more pharmaceutical agents is provided by dissolving some but not all of said amount of solid particulate in a densified fluid in the reactor.

10. The method of claim 5 wherein the one or more pharmaceutical agents comprise rifampin and minocycline.

11. The method of claim 5 wherein said polymer substrate is catheter tubing comprised of thermoplastic polyurethane elastomer or silicone elastomer, wherein said undissolved amounts are comprised of solid particulate, wherein said one or more pharmaceutical agents comprise rifampin and minocycline, and wherein the densified fluid comprises supercritical carbon dioxide.

12. A method for impregnating a polymer substrate with a pharmaceutical agent, comprising:
    contacting the polymer substrate with a first volume of densified fluid substantially saturated with one or more pharmaceutical agents, said contacting under conditions effective for impregnating the substrate with amounts of the one or more pharmaceutical agents;
    removing fluid of said first volume from the polymer substrate so as to provide the one or more pharmaceutical agents impregnated in the polymer substrate at a first level;
    contacting the polymer substrate with a second volume of densified fluid substantially saturated with the one or more pharmaceutical agents, said contacting under conditions effective for impregnating the polymer substrate with additional amounts of the one or more pharmaceutical agents; and
    removing fluid of said second volume from the polymer substrate so as to provide the one or more pharmaceutical agents impregnated in the polymer substrate at a second level higher than the first level.

13. The method of claim 12, wherein said polymer substrate is catheter tubing comprised of thermoplastic polyurethane elastomer or silicone elastomer, wherein said one or more pharmaceutical agents comprise rifampin and minocycline, and wherein the densified fluid comprises supercritical carbon dioxide.

14. The method of claim 12, wherein said removing fluid steps comprise reducing pressure on the densified fluid to evaporate the fluid.

15. The method of claim 12, wherein the first volume and the second volume comprise supercritical carbon dioxide and wherein the polymer substrate is catheter tubing comprised of thermoplastic polyurethane elastomer or silicone elastomer.

16. The method of claim 15, wherein the one or more pharmaceutical agents comprise rifampin or minocycline.

17. A method for impregnating a polymer substrate with a pharmaceutical agent, comprising:
    preconditioning the polymer substrate with a penetrating agent to provide a conditioned polymer substrate;
    contacting the conditioned polymer substrate with a densified fluid containing one or more pharmaceutical agents, said contacting under conditions effective for impregnating the polymer substrate with the one or more pharmaceutical agents; and
    wherein the penetrating agent comprises supercritical carbon dioxide free of the one or more pharmaceutical agents.

18. The method of claim 17, wherein said polymer substrate is catheter tubing.

19. The method of claim 18, wherein said catheter tubing is comprised of thermoplastic polyurethane elastomer or silicone elastomer.

20. The method of claim 17, wherein said polymer substrate has a Shore A hardness of less than 80.

21. The method of claim 17, wherein said one or more pharmaceutical agents comprise an antimicrobial agent.

22. The method of claim 21, wherein said antimicrobial agent comprises rifampin or minocycline.

23. The method of claim 22, wherein said antimicrobial agent comprises rifampin and minocycline.

24. A method for impregnating a polymer substrate with a pharmaceutical agent, comprising:
    preconditioning the polymer substrate with a penetrating agent to provide a conditioned polymer substrate;
    contacting the conditioned polymer substrate with a densified fluid containing one or more pharmaceutical agents, said contacting under conditions effective for impregnating the polymer substrate with the one or more pharmaceutical agents; and
    wherein the penetrating agent comprises supercritical carbon dioxide free of the one or more pharmaceutical agents.

25. The method of claim 24, wherein the polymer substrate is catheter tubing comprised of a thermoplastic polyurethane elastomer or silicone elastomer.

26. The method of claim 25, wherein the one or more pharmaceutical agents comprise rifampin or minocycline.

27. The method of claim 26, wherein the one or more antimicrobial agents comprise rifampin and minocycline.

\* \* \* \* \*